(12) United States Patent
Moench

(10) Patent No.: US 8,236,370 B2
(45) Date of Patent: Aug. 7, 2012

(54) CONDOMS WITH LUBRICANT COMPOSITIONS AND PACKAGING PROVIDING ENHANCED FUNCTIONALITY

(75) Inventor: Thomas R. Moench, Baltimore, MD (US)

(73) Assignee: Reprotect, Inc., Baltimore, MD (US)

( * ) Notice: Subject to any disclaimer, the term of this patent is extended or adjusted under 35 U.S.C. 154(b) by 117 days.

(21) Appl. No.: 12/307,214

(22) PCT Filed: Jul. 3, 2007

(86) PCT No.: PCT/US2007/072753
§ 371 (c)(1),
(2), (4) Date: Dec. 31, 2008

(87) PCT Pub. No.: WO2008/005986
PCT Pub. Date: Jan. 10, 2008

(65) Prior Publication Data
US 2009/0311291 A1 Dec. 17, 2009

Related U.S. Application Data

(60) Provisional application No. 60/806,599, filed on Jul. 5, 2006.

(51) Int. Cl.
| | |
|---|---|
| *A61F 6/06* | (2006.01) |
| *A61F 6/02* | (2006.01) |
| *A61F 6/04* | (2006.01) |
| *A41D 19/00* | (2006.01) |
| *B65D 85/08* | (2006.01) |
| *B65D 85/14* | (2006.01) |

(52) U.S. Cl. ......... 427/2.3; 128/830; 128/832; 128/842; 128/844; 128/917; 128/918; 206/69

(58) Field of Classification Search .............. 128/842, 128/844, 917, 918; 206/69; 514/58; 600/38–41
See application file for complete search history.

(56) References Cited

U.S. PATENT DOCUMENTS

| | | | |
|---|---|---|---|
| 5,592,949 A | 1/1997 | Moench et al. | |
| 5,617,877 A | 4/1997 | Moench et al. | |
| 6,216,697 B1 | 4/2001 | Moench et al. | |
| 6,474,338 B2 | 11/2002 | Moench et al. | |
| 6,612,427 B2* | 9/2003 | Woodhouse | 206/69 |
| 6,835,717 B2* | 12/2004 | Hildreth | 514/58 |
| 7,046,114 B2* | 5/2006 | Sakata | 336/200 |
| 7,086,403 B2* | 8/2006 | Harrison et al. | 128/844 |
| 7,316,232 B2 | 1/2008 | Moench et al. | |
| 2003/0021903 A1* | 1/2003 | Shlenker et al. | 427/385.5 |

* cited by examiner

*Primary Examiner* — Patricia Bianco
*Assistant Examiner* — Brandon L Jackson
(74) *Attorney, Agent, or Firm* — Whyte Hirschboeck Dudek S.C.

(57) ABSTRACT

The present disclosure provides improved packaged condoms that enable the use of a large quantity of a composition inside the condom. In addition, a sufficient quantity of certain spermicidal and/or microbicidal compositions is provided for efficient inactivation of sperm and pathogens. The present disclosure also provides condoms with reduced tendency to slip or break. Compositions associated with different surfaces of the condom can be effectively segregated to their intended condom surface according to the present disclosure.

25 Claims, 10 Drawing Sheets

CONDOMS WITH LUBRICANT COMPOSITIONS AND PACKAGING PROVIDING ENHANCED FUNCTIONALITY

BACKGROUND

The present disclosure relates to condoms and their use for contraception and prevention of infection. In particular, the present disclosure relates to improved compositions and packaging included with condoms to provide improved condom utility. Most condoms are packaged pre-coated with a lubricant to improve comfort during intercourse. The lubricant may also include agents that provide other beneficial functions, such as desensitizers, spermicides, or microbicides—agents that inactivate or otherwise block infection by sexually transmitted pathogens, including HIV.

The amount of lubricant that has been included with condoms is generally low, particularly on the inner condom surface. As demonstrated in Table 1 below, the inner condom surface of typical commercially available condoms has less than one gram of a lubricant composition.

TABLE 1

| Condom | A. Weight of intact package (grams) | B. Weight of lubricant on inner condom surface * (grams) | C. Weight of condom and package after washing and drying ** (grams) | D. Weight of lubricant A-C (grams) |
|---|---|---|---|---|
| TROJAN ENZ ®, lubricated | 3.38 | 0.23 | 2.79 | 0.59 |
| TROJAN EXTENDED PLEASURE ® | 3.83 | 0.57 | 2.69 | 1.14 |
| TROJAN ULTRA PLEASURE ® | 3.31 | 0.11 | 2.90 | 0.41 |
| KIMONO MICROTHIN ® | 2.45 | 0.12 | 2.01 | 0.44 |
| LIFESTYLES ULTRA SENSITIVE ® with Spermicide | 2.80 | 0.14 | 2.29 | 0.51 |
| DUREX AVANTI ® | 2.99 | 0.10 | 2.37 | 0.62 |
| DUREX PERFORMAX ® | 3.17 | 0.33 | 2.48 | 0.69 |
| MEDTECH INSPIRAL ® | 4.29 | 0.17 | 3.71 | 0.58 |

\* Determined by weighing lubricant wiped off with an absorbent tissue.
\*\* Determined by washing condom and package with detergent, rinsing, and drying in a ventilated oven at 40 degrees C.

In addition, typical spermicides and/or microbicides are sufficiently potent to inactivate pathogens and sperm in an entire ejaculate of semen at quantities of less than or equal to several tenths of a gram. Thus, spermicides and/or microbicides function well when present as a small fraction of the volume of a typical ejaculate. However, the spermicidal and microbicidal agents presently used on condoms are non-selective detergents that are highly potent and can be toxic to genital tract epithelium and may paradoxically result in increased susceptibility to infection. Compositions including spermicidal and microbicidal agents are often applied to the inner surface of a condom where the composition can immediately mix with semen after ejaculation and is not wiped off during penile intromission.

Although the small quantities (less than 0.6 grams, as illustrated in Table 1) of lubricant compositions present on the inner surface of commercially available condoms are often adequate due to their high potency, some agents provide benefits at increased quantities. Also, to maintain efficacy of certain agents found in minimally dilutable compositions, increased quantities of the composition must be packaged with condoms. For example, acidic buffering agents are far less toxic to epithelial surfaces but must be present in amounts representing a substantial fraction of the quantity of semen in an ejaculate to be effective.

Known compositions and packaging elements included with condoms present problems associated with providing increased quantities of a composition to the inside of a condom. These problems include insufficient space to load the increased quantity of the composition on the inner surface of the condom. Also, the composition, once loaded, may not be well retained where needed due to the force of gravity or the forces caused by accelerations and decelerations acting on the composition during storage, transport, removal, or application of the condom.

Lubricants are generally applied by the manufacturer to one or both sides of the closed end of the condoms after the condoms are rolled up over the majority of their length, yet the lubricant redistributes over at least the first one to three inches of the condom length because, as illustrated in FIG. 1, the lubricant 12 propagates by capillary action into the spiral space 14 between layers of the rolled portion of the condom 10. Whether or not the lubricant is intentionally applied to both sides, propagation of the composition into this spiral space inevitably results in lubricant contacting both inner surface 16 and outer surface 18 of the condom 10, since this spiral space 14 is bounded by the inner surface 16 on one side and the outer surface 18 on the other side.

Furthermore, the viscosity of these compositions decreases even further during use due to the hypertonicity of the compositions. In particular, high concentrations of low molecular weight compounds, such as polyethylene glycol, glycerol, and propylene glycol, tend to draw water out of the penile skin, thereby diluting the composition and lowering its viscosity to further exacerbate the tendency of the condom to slip from the penis. Providing a large quantity of the type of composition typically provided with condoms may make the condom even more likely to slip due to the composition's low viscosity, and due to the ease with which a large quantity of the composition would spread to cover an excessively large portion of the condom during use.

Another well-known problem is that condoms sometimes break or slip off the penis during use. Although condoms are known to be effective contraceptives and effective at blocking the transmission of sexually transmitted infections including HIV, slippage and breakage of the condoms reduces the effectiveness of their intended barrier function, exposing each sexual partner to the potentially infectious secretions of the other partner. The risk of cervicovaginal exposure to sperm will also increase when condoms break or slip when being used as contraceptives.

Both slippage and breakage of condoms generally result from stresses placed on the condom during use that may cause them to stretch to the point of breakage or to slip partially or completely off the penis. The risk of condom breakage is made greater under circumstances where the inner surface of the condom is poorly adherent to and tends to slip against the penis when viscous drag at the outer surface of the condom causes stress to the condom that might cause it to stretch and break. This problem is exacerbated by low viscosity substances on the inner surface of the condom, such as an internal composition provided with the condom or deposition of semen post-ejaculation.

Condom slippage is also exacerbated by the exposure of the inner surface of the condom to low viscosity substances such as a lubricant provided with the condom and semen. Upon ejaculation, a substantial volume of semen, typically 1 to 6 mL, is deposited within the condom, and is widely distributed throughout the space between the inner surface of the condom and the penis to cover a large fraction of the inner surface of the condom. Due to the low viscosity of liquefied semen, the semen acts as a low viscosity lubricant to increase the tendency of a condom to slip off the penis after ejaculation.

Adherence of a condom to a penis can reduce slippage and breakage and is determined by multiple factors. The factors include size and shape of the condom relative to the penis, and, thus, the degree of compressive force with which the condom grips the penis due to the elastic forces in the condom. Attempts to prevent condom slippage include manufacturing condoms having a high coefficient of friction at its inner surface, condoms with an adhesive band near its open end, and condoms having a constricted region with decreased diameter to grip the penis more tightly at that region. However, condoms are available in a limited number of shapes and sizes. Moreover, if penile detumescence occurs before withdrawal, the reduction in penile size reduces the degree of compressive force with which the condom grips the penis, increasing the chance of the condom slipping off during withdrawal. Therefore, it would be advantageous to provide improved condom adherence to the penis that is independent of the relationship between the size and shape of the condom and that of the penis.

There is therefore a need for improved compositions and methods of preventing condom slippage and delivering increased quantities of a composition containing a beneficial agent.

SUMMARY

The present disclosure relates to improvements in condom function and reliability. In particular, the present disclosure relates to providing an increased quantity of a composition to the inner surface of a condom, referred to herein as an inner composition. The present disclosure also relates to enabling an increased quantity of an inner composition to be delivered to a user via the inner surface of a condom. In order to make application of increased quantities of an inner condom surface composition feasible, an inner composition is provided with a rheological character that allows reliable retention of this large quantity of inner composition on the inner surface during the unwrapping and application of the condom, when conventional compositions easily run or drip off. In certain embodiments, packaging elements are employed to provide sufficient space for the larger quantity of inner composition to be more easily accommodated and retained. In another embodiment, the quantity and character of the inner composition is chosen to reduce the tendency of the condom to slip off during intercourse or upon withdrawal. In additional embodiments, a second composition is also provided on the outer surface of the condom (an "outer composition"). In another embodiment, packaging elements are employed to confine the inner composition to the inner surface of the condom, and the outer composition, if any, to the outer surface of the condom.

To this end, in an embodiment, a penile barrier device is provided. The penile barrier device includes a condom having an inner surface and an outer surface and a first composition. The first composition has a viscosity between about 100 and 10,000 mPa-s measured at a shear rate of 500 per second, and a viscosity of at least about 2 million mPa-s measured at a shear rate of 0.001 per second. More than one gram of the first composition is disposed along at least a portion of the inner surface of the condom.

In an embodiment, the first composition has a viscosity between about 200 and 5,000 mPa-s measured at a shear rate of 500 per second.

In an embodiment, the first composition has a viscosity between about 400 and 2,000 mPa-s measured at a shear rate of 500 per second.

In an embodiment, the first composition has an osmotic strength of less than about 600 mOsm.

In an embodiment, the first composition is in the form of a gel.

In an embodiment, the composition includes an acid buffer.

In an embodiment, the acid buffer includes a cross-linked polyacrylic acid.

In an embodiment, the cross-linked polyacrylic acid includes a carbomer.

In an embodiment, the first composition includes an agent selected from the group consisting of a contraceptive, a microbicide, a lubricant and combinations thereof.

In an embodiment, a second composition is disposed along at least a portion of the outer surface of the condom, wherein the second composition has a viscosity of less than about half the viscosity of the first composition measured at a shear rate of 500 per second.

In an embodiment, the second composition has a viscosity of at least 2 million measured at a shear rate of 0.001 per second.

Another embodiment of the present disclosure includes a kit. The kit includes a condom having an open end and a closed end at opposing ends of a length of the condom, with an inner surface and an outer surface. The open end of the condom is rolled over a substantial portion of its length to form a condom ring having a circumference. The kit also includes a first composition having a viscosity of between 100 and 10,000 measured at a shear rate of 500 per second and a viscosity of at least 2 million measured at a shear rate of 0.001 per second. At least one gram of the first composition is disposed on at least a portion of the inner surface of the condom. The kit further includes a package having a cavity defined by a closed end support surface and a ring support structure separated by a separation distance between the closed end support surface and the ring support structure. The closed end of the condom is oriented toward the closed end support surface and the open end of the condom is oriented toward the ring support structure. The ring support structure is adapted to support the condom ring of the open end of the condom in a position at the separation distance from the closed end of the condom, such that the first composition is substantially retained on at least a portion of the inner condom surface.

In an embodiment, the separation distance is between about 1 to about 12 mm.

In an embodiment, the kit is removably enclosed within an enclosure package.

In an embodiment, the closed end support surface forms at least a portion of the enclosure package.

In an embodiment, the package comprises a material having a moisture vapor transmission rate of less than 0.01 grams/square meter/24 hours.

In an embodiment, the package includes at least one packaging element adapted to provide circumferential compression of the ring.

In an embodiment, the packaging element includes a ring support structure.

In an embodiment, the circumferential compression is directed inward. In an embodiment, the kit includes a second composition associated with an outer surface of the condom, the second composition having a viscosity of at least 1 million measured at a shear rate of 0.001 per second, and a viscosity measured at 500 per second less than half that of the first composition, such that the second composition avoids contact with the spiral space between overlapping layers of the condom in the ring.

In an embodiment, the package is adapted to removably secure the condom to enable a user to position the condom in a proper orientation onto the glans of the penis before removing the package from the condom.

A further embodiment of the present disclosure includes a method of delivering an effective amount of a beneficial agent to a penis. The method includes providing the beneficial agent in a composition having a viscosity of between 100 and 10,000 measured at a shear rate of 500 per second, and a viscosity of at least 2 million measured at a shear rate of 0.001 per second. The method also includes associating more than one gram of the composition with the inner surface of a condom. The method further includes applying the condom to the penis.

In an embodiment, the composition includes an agent selected from the group consisting of a contraceptive, a microbicide, a lubricant and combinations thereof.

In an embodiment, the method includes providing condom packaging adapted to maintain a separation distance between an open end of the condom and a closed end of the condom such that the composition is substantially retained within the lumen of the condom.

Yet another embodiment of the present disclosure includes a method of minimizing the movement of a condom on a penis during sexual intercourse wherein the condom contains more than one gram of a composition associated with an inner surface of the condom in contact with the penis. The method includes formulating the composition to have a viscosity of between 100 and 10,000 measured at a shear rate of 500 per second, and a viscosity of at least 2 million measured at a shear rate of 0.001 per second.

It is therefore an advantage of the present disclosure to provide a condom with an increased quantity of a beneficial composition.

Another advantage of the present disclosure includes providing an increased quantity of a beneficial composition without compromising retention of the composition in a desired location during packaging, shipping, handling, storage and use.

A further advantage of the present disclosure includes reducing slippage and breakage of condoms during use.

Yet another advantage of the present disclosure is to provide packaging of a condom that allows an increased quantity of a composition to be delivered with the condom.

An additional advantage of the present disclosure includes providing condom packaging that enables a user to properly position the condom for donning of the condom.

Additional features and advantages are described herein, and will be apparent from, the following Detailed Description and the figures.

DETAILED DESCRIPTION

Figure 1:
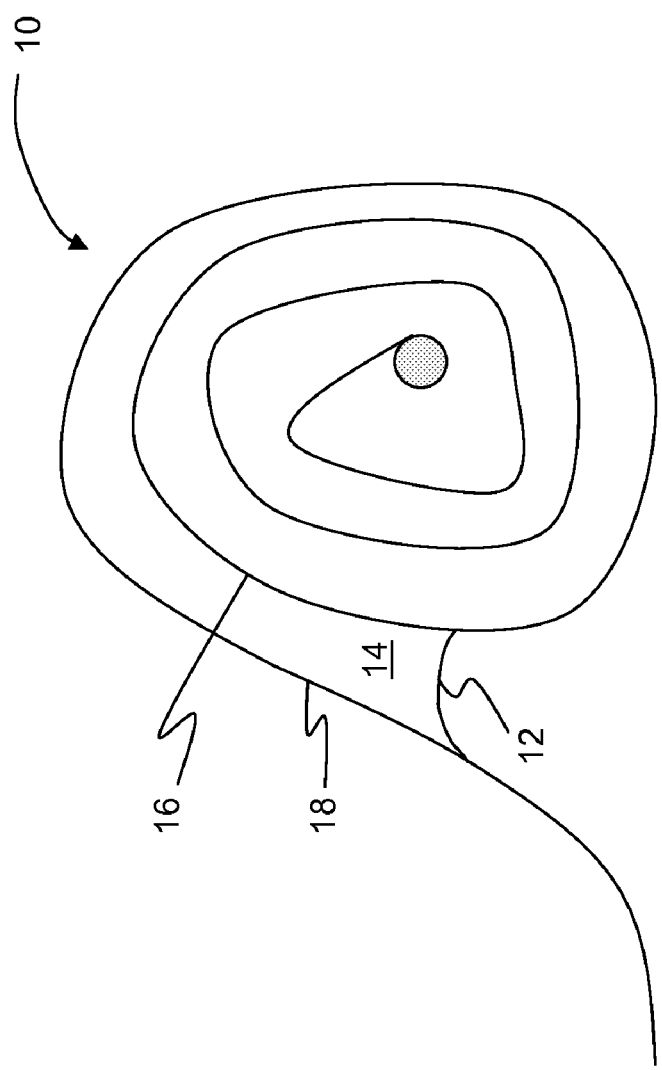
FIG. 1 is a side view of the rolled portion of a condom of an embodiment described in the present disclosure.

The present disclosure relates to an improved composition and method of delivering an increased quantity of a beneficial substance associated with a condom while minimizing condom slippage. In particular, the present disclosure relates to providing a beneficial substance having a substantially high viscosity at a substantially low shear rate, and a substantially low viscosity at a substantially high shear rate. It has been surprisingly found that substances having these rheological characteristics allow delivery of the substance to a desired area while maintaining proper retention of the substance within the condom during storage and use, preventing condom slippage during use.

In an embodiment, an increased quantity (in relation to that used in the prior art) of a composition is provided in association with an inner surface of a condom. The composition may be in the form of a gel, salve, ointment cream or any other suitable semi-solid form. As used herein, the term gel refers to a colloid in which the disperse phase combines with the dispersion medium to produce a semi-solid material. The gel may include any suitable characteristics and combinations thereof, such as being an inorganic or organic chemical composition, including water or an organic solvent as a liquid component, being colloidal or coarse depending on the size of the particles forming the framework, and being rigid, elastic, or thixotropic.

The gel may act as a lubricant. As used herein, the term "lubricant" or "composition" refers to non-solid compositions with lubricant characteristics. It should be appreciated, that an increased quantity of the gel may provide other beneficial functions. For example, providing an unusually large quantity of a composition, particularly to the inside surface of a condom, may cause the composition to be distributed over an advantageously large portion of the penis. Also, the composition may include a spermicidal agent, a microbicidal agent, or any other beneficial agent. To this end, the gel may be particularly well suited to deliver a spermicidal agent or a microbicidal agent that is particularly effective when administered in a quantity of greater than 0.6 grams.

Accordingly, an increased quantity of the inner composition is provided disposed along at least a portion of the inner surface of a condom. The quantity of gel included with the inner surface of the condom may include more than 0.6 grams, between about 1 and 6 grams, or between about 2 and 3 grams.

In addition to providing an increased quantity of a composition associated with a condom, in an embodiment, the composition has a viscosity that is strongly dependent on shear rate. Therefore, in an embodiment, a composition is provided having a relatively high viscosity at relatively low shear rates and relatively low viscosity at relatively high shear rates. A composition having a high viscosity at low shear rate increases the resistance of the composition to migration or movement when the condom is not in use, and the same composition having a viscosity many orders of magnitude lower at the higher shear rates experienced during sexual intercourse, allows subtle movements of the condom over the penis during intercourse sufficient to enhance sensation and pleasure.

As used herein, the term shear rate refers to the rate of deformation of a substance in which parallel internal surfaces slide past one another. In particular, the shear rate of the inner composition is defined as the speed of displacement (cm/sec) divided by the separation distance (cm) between two moving surfaces separated by the inner composition. Thus, the units associated with shear rate can be inverse seconds, or "per second".

Very low shear rates can include the shear rates that are relevant to predicting behavior of gels as they drip or creep slowly under the influence of gravity or other modest accelerations or decelerations as are experienced during shipping and handling of the condom. Such a shear rate is lower than that which can be produced with the use of standard viscometers, which are typically limited to about 0.1 per second, but can be assessed with alternative techniques that can measure viscosity at a shear rate of 0.001 per second and below.

High shear rates refer to shear rates typical of sexual intercourse. The shear rate typical of sexual intercourse is estimated as a linear penile displacement rate of 25 cm/sec relative to a mucosal surface and a separation distance of 0.05 cm (the estimated thickness of a lubricant and/or sexual mucus secretions separating a surface of the condom from the penis or other sexual partner). Accordingly, a shear rate typically experienced by the lubricant during intercourse is estimated at about 25 cm per second/0.05 cm=500 per second.

As used herein, the term viscosity refers to the resistance of a fluid to flow acting against the motion of any solid object through the fluid, against the motion of the fluid itself past stationary obstacles and against the motion of adjacent layers of the fluid internally. In an embodiment, the gel may have a viscosity of at least about 2 million mPa-s, and more particularly between about 10 million mPa-s and about 40 million mPa-s, at a shear rate of approximately of 0.001 per second. This property of the composition advantageously assures that the rate at which the composition creeps or drips under the influence of gravity or other accelerations or decelerations during storage and donning of the condom is so slow that the composition will be well retained.

It is also advantageous to include an inner composition having a relatively low viscosity at shear rates characteristic of sexual intercourse to prevent the inner composition from reducing sensation by preventing the subtle motion of the condom against the penis during intercourse. Therefore, the upper limit of the viscosity of the inner composition may be less than about 10,000 mPa-s, less than about 5000 mPa-s, or below about 1000 mPa-s at a shear rate of 500 per second. Limiting the viscosity of the composition at shear rates typical of sexual intercourse advantageously assures that the composition does not reduce sensation by interfering with subtle motion of the inner surface of the condom relative to the skin.

The viscosity of various types of compositions over a wide range of shear rates and the rheological characteristics of compositions are illustrated in the following examples.

EXAMPLE 1

A variety of compositions listed in Table 2 below, along with their respective viscosity-generating agents, were assessed by two viscosity tests and two tests of "vertical cling" described in further detail below. BUFFERGEL®, for example, is a microbicidal spermicide whose viscosity is determined by the following features in its formula: 3.8% carbomer 974P, anhydrous $K_2HPO_4$ added in quantity sufficient to adjust the pH to 3.85 (generally 0.8 to 1.2% w/w), and an appropriate amount of $MgSO_4 \cdot 7H_2O$, (such as between 0.01 and 0.25% (w/w)) to further adjust viscosity. A series of simple variants of the BUFFERGEL® formulation with different viscosities were created by diluting BUFFERGEL® with normal saline (0.9% sodium chloride in water) to the proportions shown. Other compositions tested include commercially available lubricants, condom lubricants, and ingredients commonly used as viscosity generating agents in lubricant formulations.

TABLE 2

| Composition | Viscosity generating agent(s) |
|---|---|
| BUFFERGEL ® (ReProtect, Inc) | Carbomer 974P |
| BUFFERGEL ® 90%, normal saline 10% | Carbomer 974P |
| BUFFERGEL ® 80%, normal saline 20% | Carbomer 974P |
| BUFFERGEL ® 75%, normal saline 25% | Carbomer 974P |
| BUFFERGEL ® 70%, normal saline 30% | Carbomer 974P |
| REPHRESH ® (Li'l Drug Store Products, Inc.) | Polycarbophil, Carbomer 934P, Glycerin |
| GYNOL II ® Extra strength (Personal Products Company) | Carboxymethylcellulose, Propylene glycol |
| CONCEPTROL ® (Personal Products Company) | Sodium carboxymethylcellulose, Propylene glycol |
| K-Y ® Jelly (Personal Products Company) | Hydroxyethylcellulose, Glycerin |
| PRE-SEED ® (INGFertility) | Hydroxyethylcellulose, Carbomer 934 |
| TROJAN ENZ ® condom lubricant (Carter Wallace) | |
| K-Y ® Liquid (Personal Products Company) | Hydroxyethylcellulose, propylene glycol |
| K-Y ® Warming ULTRAgel (Personal Products Company) | Hydroxypropylcellulose, propylene glycol, polyethylene glycol |
| ASTROGLIDE ® (BioFilm, Inc.) | Glycerin, Propylene glycol, Polyquaternium |
| Glycerin (J. T. Baker) | Glycerin |
| Polyethylene glycol (Fischer Scientific) | Polyethylene glycol |
| Silicone fluid (General Electric Co.) | Dimethylpolysiloxane |
| H-R Lubricant (Carter Wallace) | Hydroxypropylmethylcellulose, Carbomer 934P, Propylene glycol |

Figure 2:
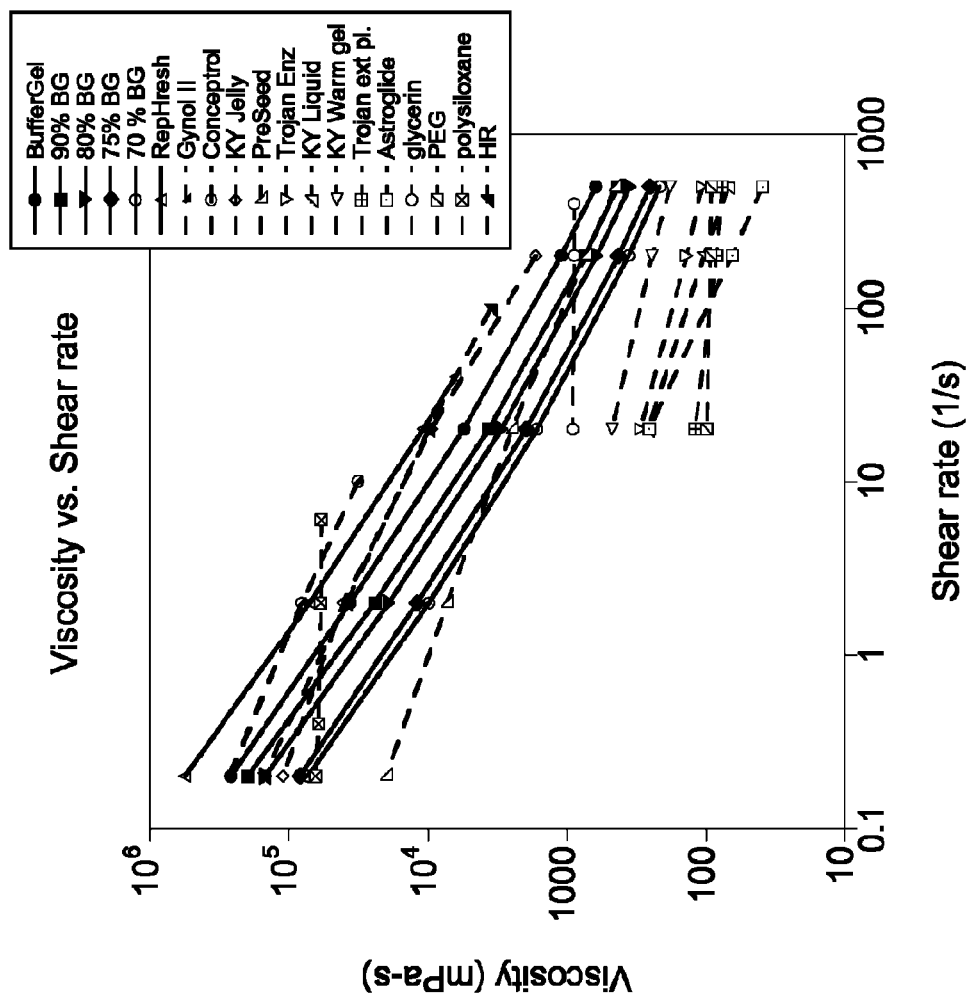
FIG. 2 is a plot comparing log viscosity to log shear rate for various compositions described in the present disclosure.

Referring to FIG. 2, in the first viscosity test, measurements were made of the viscosities of various compositions over a range of shear rates from 500 per second to 0.1 per second, except as limited for certain compositions by the torque range of the instrument. The first viscosity test was performed using a Brookfield Model HADV-III Programmable cone and plate rheometer and a CP52 conical spindle (radius 1.2 cm, angle 3 degrees) at 25 degrees centigrade, and 0.5 mL sample volume. Results are displayed in FIG. 2 as a plot comparing log viscosity to log shear rate. It will be appreciated that the plots of log viscosity as a function of log shear for the compositions show three distinct patterns distinguished by their slope.

One type of slope illustrated in FIG. 2 includes a line with near zero slope, indicating that viscosity is independent or nearly independent of shear rate. Such a slope is characteristic of Newtonian fluids such as water, oils, and fluids comprising small molecules such as glycerin, sugars, other polyols, and short polymers such as polyethylene glycol, or aqueous solutions thereof. Accordingly, as indicated in FIG. 2, compositions including polysiloxane, glycerin, polyethylene glycol, and TROJAN EXTENDED PLEASURE® condom lubricant have a substantially flat line and essentially no slope.

The second type of slope illustrated in FIG. 2 includes a straight or nearly straight line with a gradual downward slope indicating a moderate reduction of viscosity with increasing shear rate. Such a slope is characteristic of compositions having a viscosity created mainly by the inclusion of various modified cellulose polymers such as hydroxymethylcellulose, hydroxypropylcellulose and the like. These compositions demonstrate "shear thinning", a progressive drop in viscosity with increasing shear rates. Although moderately steep, these compositions are substantially less steep than those compositions showing the third type of slope (see below). Examples of compositions having a moderately decreasing slope as indicated in FIG. 2 include GYNOL II®, CONCEPTROL®, K-Y® jelly, PRE-SEED®, TROJAN ENZ® condom lubricant, K-Y® liquid, K-Y® Warming ULTRAgel®, TROJAN EXTENDED PLEASURE® condom lubricant, ASTROGLIDE® and H-R® Lubricating Jelly.

The third type of slope illustrated in FIG. 2 includes a straight or nearly straight line, shown with solid lines, having a substantially steeper downward slope than the other compositions. The compositions depicted with the solid lines also demonstrate shear thinning, but to a substantially greater degree than those indicated in FIG. 2 with the dotted lines. Examples of compositions having a steep downward slope as illustrated in FIG. 2 include BUFFERGEL®, 90% BUFFERGEL®, 80% BUFFERGEL®, 75% BUFFERGEL®, 70% BUFFERGEL®, and REPHRESH®. It is notable that compositions showing this third type of slope, with considerably greater steepness than the other compositions, are formulated using polymers such as cross-linked polyacrylic acids and the like as their viscosity-generating components. However, it is also notable that not all of the compositions that contain cross-linked polyacrylic acids show this steepest slope. Specifically, HR LUBRICANT® and PRE-SEED® contain cross-linked polyacrylic acids, have only moderate slope.

The property of very high viscosity at low shear rate endows compositions with the third type of slope with a robust anti-drip, anti-creep character that allows it to be well retained on the inner surface of the closed end of a partially rolled condom, even when an increased quantity of this type of composition is employed. Such a high quantity of any of the common condom lubricant compositions would otherwise easily drip off or be otherwise displaced as the condom is donned, or might move undesirably during handling shipping or storage, where even slow movements become cumulatively large over time.

It should be appreciated that the shear rates characteristic of the slow movement of gel compositions under relatively modest forces, such as those experienced when a gel-coated condom is handled, shipped, stored in various orientations, or manipulated during donning, will, at times, be even lower than the minimum shear rate of about 0.1 per second that can be produced with the standard methods. Viscosity at shear rates below 0.1 per second, however, are relevant to the choice of compositions provided in large volume and retained where placed on the condom. For this reason, the viscosities of a subset of the compositions in Table 2 were measured at shear rates less than 0.1 per second by the spring-relaxation technique described below.

EXAMPLE 2

Behavior of compositions under low but still relevant shear rates were measured using a spring-relaxation technique known in the art, using a Brookfield HADV-III® cone and plate viscometer with a spring strength at full excursion of 14,374 dyne-cm. A CP40 conical spindle was used, with a radius of 2.4 cm, and an angle of 0.08 degrees. The sample volume was 0.5 mL, and temperature was held at 25 degrees centigrade with a circulating water bath. The motor was run for one minute at a rate that produced full winding of the spring, or, if full winding could not be achieved, at maximum RPM (250 RPM). The motor driving the rotating spindle of the viscometer was switched off, and the spindle was then driven by the residual torque in the viscometer's torque-indicating spring. When rotated only by the progressively diminishing residual spring tension, the rate of rotation of the spindle soon becomes extremely low, producing low shear rate by this progressively slowing rotation. The torque readings recorded as a function of time are plotted in FIG. 3.

Shear rate and viscosity are calculated at various intervals by recording the torque readings as a function of time. Shear rate is calculated according to the formula: Shear rate (in inverse seconds)=SRC*RPM (where * means multiplied by). SRC is the Shear Rate Constant (7.5 for the CP40 spindle). Spindle speed (RPM) is calculated by noting the change in torque during each interval of interest, and converting this to revolutions according to the appropriate conversion factor for the HADV-III viscometer: each 1% change in torque corresponds to 0.00208 revolutions. The number of revolutions is then divided by the time interval in minutes. Viscosity during an interval of interest is calculated according to the formula: Viscosity (in mPa-s)=(100/rpm)*TK*SMC*Torque, where TK is the spring constant for the viscometer (here 2.0), SMC is the Spindle Multiplier Constant (here 0.327), and Torque is the mean of the beginning and ending torque of the interval. Shear rate and viscosity were measured for three intervals for each composition, plotted, curve fit to a power function ($y=a*x^b$), and viscosities for shear rates of 0.001 and 0.0001 per second were interpolated or extrapolated and recorded in Table 3 below.

Figure 3:
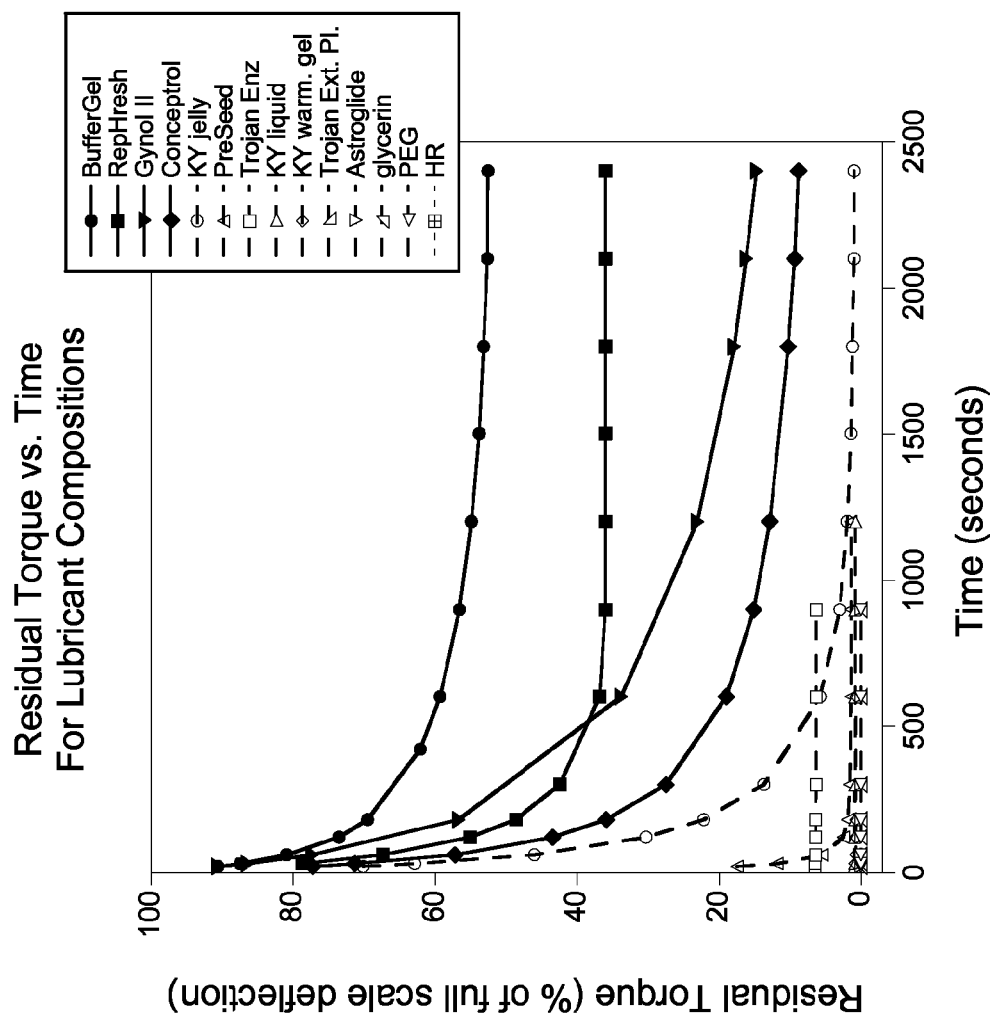
FIG. 3 is a plot comparing the percent residual torque to time after turning off the motor driving the viscometer spindle contacting compositions described in the present disclosure.

FIG. 3 is a plot of the torque readings of the spring relaxation technique applied to the compositions plotted against time. It shows great differences between compositions in the degree to which the various compositions can resist the very modest shear stress applied by the unwinding spring driving the spindle. For example, two compositions, BUFFERGEL® and REPHRESH®, both containing cross-linked polyacrylic acids show remarkable ability to resist the unwinding of the spring, as evidenced by their holding a constant torque after brief initial torque decreases. This suggests a very high viscosity at low shear, as confirmed in Table 3 where the calculated viscosities at 0.001 and 0.0001 per second shear rates are listed. Two additional compositions (GYNOL II® Extra Strength, and CONCEPTROL®, with cellulosic gelling agents) show some resistance to spindle rotation, though substantially less than the cross-linked polyacrylic acid compositions and the like. The viscosities shown in Table 2 confirm that, though their viscosities at low shear are large, they are not nearly as large as the cross-linked polyacrylic acid compositions. This indicates that compositions with high levels of residual torque for more than about 1000 seconds can effectively resist a considerable shear stress without giving way, and that the cross-linked polyacrylic acids show the greatest resistance.

EXAMPLE 3

A subset of the compositions described in Table 2 was also tested in two assays to assess "vertical cling". In the first assay, 2 grams of the composition was distributed over a two-centimeter diameter spot on an unlubricated TROJAN ENZ® condom that had been washed in tap water, dried, and pulled onto a 3 cm diameter cylindrical mandrel. The mandrel, with its enveloping condom, and applied composition was rotated to vertical, and then movement of the lower edge of the composition was observed for 10-second and 10-minute time periods. Compositions that moved less than 1 cm after 10 seconds were judged to have shown sufficient vertical cling to predict that the composition would resist drip-off during donning of a condom and were scored as having passed the 10-second test. Compositions that moved less than 1 cm after 10 minutes were judged to have shown sufficient vertical cling to predict the composition would resist movement during storage and handling of packaged condoms, and were scored as having passed the 10-minute test. Results are shown in Table 3, which also contains the spring relaxation viscosity values.

TABLE 3

| Test | BUFFERGEL® | REPHRESH® | GYNOL II® ES | CONCEPTROL® | K-Y® Jelly | PRE-SEED® | K-Y® Liquid | ASTROGLIDE® |
|---|---|---|---|---|---|---|---|---|
| 10 sec vertical-cling test | Pass | Pass | Pass | Pass | Fail | Fail | Fail | Fail |
| 10 min vertical-cling test | Pass | Pass | Fail | Fail | Fail | Fail | Fail | Fail |
| Viscosity at shear rate of 0.001 | 27 million | 17 million | 4 million | 4 million | 700,000 | 800,000 | <1000 | <1000 |
| Viscosity at shear rate of 0.0001 | 270 million | 160 million | 13 million | 20 million | 2 million | 5 million | <1000 | <1000 |

Comparing the results of the vertical cling test in Table 3 with the measurements of viscosity at very low shear rates (0.001 and 0.0001 per second), it should be appreciated that there is a good correlation between the vertical cling tests, and the viscosity at very low shear rates. It should also be appreciated that compositions that passed the more rigorous vertical cling tests (10 minutes) are those with extraordinarily high viscosity at low shear rate.

Viscosity-generating agents that provide a sufficient slope (i.e., those depicted with solid lines) on the plot in FIG. 2 may be used to obtain a substantial difference in viscosity at two substantially different shear rates. Materials used in the disclosed compositions to achieve the appropriate viscosities at both the specified shear rates may include carbomers such as Carbopols® manufactured by Noveon, Inc., polycarbophil, (Noveon® AA-1 polycarbophil, Noveon, Inc.) and any other suitable cross-linked polyacrylic acids. Cross-linked polyacrylic acids may be used to produce pharmaceutically acceptable vehicles for a wide range of active ingredients, and can be used in acid buffering compositions suitable for use as spermicidal microbicides. Other polymers having similar properties may also be used such as polymethacrylate, glyceryl polymethacrylate and the like. In addition, polymers such as carboxymethylcellulose or other linear polymers may also be used to produce the suitable range of viscosities at the shear rates described herein. These viscosity-generating agents may be used in combination with, or in addition to, other disclosed polymers and compositions discussed above, including relatively low molecular weight substances such as glycerin, propylene glycol, and polyethylene glycol.

Comparison of FIG. 2 with the viscosity values in Table 3 also show that the steepness of slope characteristic of the compositions plotted in FIG. 2 correlate well with viscosities recorded at very low shear rates (0.001 and 0.0001). Furthermore, both the slopes shown in FIG. 2, and the low shear rate viscosities of Table 3 correlate with the non-drip/vertical-cling tests in Table 3. Thus, all three of these methods used to assess the rheological characteristics of a composition are helpful in predicting which compositions are suitable to be provided in unusually high quantity on the inner surface of a condom.

Achieving the disclosed advantageous viscosities at both high and low shear rates may be obtained by adjusting the concentration of the viscosity-enhancing agent, the formulation pH, and the concentrations of ionizable salts. Examples of ranges of these parameters that yield compositions with the desired viscosities at both the high and low shear rates are provided below:

For a given gelling or thickening agent, viscosity at a given shear rate may be adjusted by changing the concentration of the agent chosen according to the principles outlined above. Although some resistance to creep or dripping can be obtained by employing very high concentrations of polymers such as carboxymethylcellulose or other linear polymers, achieving a robust non-drip character (extraordinarily high viscosity at low shear rate) particularly to resist movement of the composition within the packaging, is difficult to achieve, and if achieved, may result in an excessively high viscosity at the shear rates typical of intercourse.

The viscosity produced by compositions employing cross-linked polyacrylic acids and the like may be pH dependent, that is, lower viscosities may be obtained by formulating the composition at a lower pH. For example, when such compositions are formulated with a pH below about 4, relatively high concentrations of cross-linked polyacrylic acid polymers and the like may be used to obtain the appropriate viscosities. The composition may include about 2% to about 8% polyacrylic acid, or about 3.5% to about 8% polyacrylic acid.

When the function of the composition is dependent on activity provided by the acid buffering capability of the composition, as in BUFFERGEL®, it may be advantageous to use relatively high concentrations of one or more cross-linked polyacrylic acids. Cross-linked polyacrylic acids may be advantageously included in the range of, for example, about 3% to about 8% total polyacrylic acid, or about 3.8% to about 6%. A low pH may be used for this type of composition, namely, in the range of about 2.5 to about 4.5, or from about 3.5 to about 3.9.

When the composition pH is above 4, lower concentrations of the viscosity-generating polymer may provide the appropriate viscosities including, for example, concentrations of about 0.25% to about 2%, or about 0.5% to about 1.5% cross-linked polyacrylic acids.

pH may be adjusted by simple titration to the desired endpoint with various alkalinizing agents known in the art, such as sodium hydroxide, potassium hydroxide, dibasic potassium phosphate, dibasic sodium phosphate, dibasic sodium or potassium citrate, tribasic sodium or potassium citrate, triethanolamine, or other neutralizing agents.

Viscosity may also be influenced by the presence of other materials, particularly ionizable materials such as various salts containing monovalent, divalent, or trivalent cations, which will decrease viscosity. Ionizable materials may be employed to adjust tonicity, to adjust viscosity, or to provide any other beneficial effects. However, excessive amounts of salts may excessively reduce viscosity. Divalent cations in ratios that exceed about 0.01 to about 0.1 gram of cation per gram of cross-linked polyacrylic acid may cause disadvantageous reductions in viscosity, depending on the particular divalent cation, the type of cross-linked polyacrylic acid, and the formulation pH. Likewise monovalent cations in ratios of between about 0.1 and about 1 gram per gram of polymer may cause disadvantageous reductions in viscosity, depending on the particular monovalent cation, the type of cross-linked polyacrylic acid, and the formulation pH.

Failure to achieve the desired viscosities may be due to inappropriate concentration of cross-linked polyacrylic acid, inappropriate pH, or excessive concentration of ionizable salts. For example, although two of the compositions shown in FIGS. 2 and 3, PRE-SEED INTIMATE MOISTURIZER® and H-R® Lubricating Jelly, contain a viscosity-generating agent (specifically Carbopol® 934), the compositions fail to provide the desired viscosities. These compositions may fail to provide the desired viscosities because of inadequate concentrations or type of the viscosity-generating agent, the pH of the formulation, concentration of ionizable salts in the formulation or because of other disadvantageous components.

In contrast, the concentration of the viscosity-enhancing agent, the formulation pH, and the concentrations of ionizable salts are adjusted in compositions such as BUFFERGEL® to produce an appropriate viscosity at both low and high shear for the practice of the present invention. In particular, BUFFERGEL® includes a concentration of 3.8% of a cross-linked polyacrylic acid (carbomer 974P), with the pH adjusted to approximately 3.85 with dibasic potassium phosphate added in a quantity sufficient (approximately 1% w/w) to reach this pH, tonicity adjusted with monobasic sodium phosphate 0.1 to 0.5% w/w, and with the viscosity further adjusted with $MgSO_4 \cdot 7H_2O$ (range 0.01-0.2% w/w). Additional desirable formulation characteristics are provided by other components (namely, preservatives, and chelators) but these do not have strong effects on the final high and low shear viscosities.

As discussed above, other viscosity-enhancing agents may include cellulosic polymers, such as carboxymethylcellulose, hydroxyethylcellulose, hydroxypropylmethylcellulose, hydroxypropylcellulose, and methylcellulose. Cellulose-based compositions may provide appropriate viscosities when used at concentrations between about 1 and about 4%. Cellulose-based compositions may at least provide sufficient viscosity at low shear to prevent loss of an inner composition upon condom donning. Cellulose-based compositions may not be as dependent on ionic components or pH to affect the viscosity of such compositions to the degree as in compositions including other polymers such as cross-linked polyacrylic acid.

In an embodiment of the invention, the adherent contact between the inner surface of the condom and the penis may be further enhanced by selection of an inner composition that exhibits at least a degree of bioadhesiveness such as cross-linked polyacrylic acid polymers including carbomer and polycarbophil. As referred to herein, the term "bioadhesiveness" indicates a property of certain compositions that improves their adherence to biological surfaces. In addition to adhesiveness to mucosal surfaces, bioadhesive materials also adhere well to skin. Thus, bioadhesiveness may be an advantageous quality for an inner adherent composition intended to adhere well to the penis.

In order to increase the ease with which an effective quantity of a composition may be controlled, such as during the step of placing the condom on the penis, the condom tip may be designed to aid in this process. For example, a quantity of at least 3 mL of the composition may be accommodated in a reservoir tip or nipple of the condom. At least a portion of the gel may be held within the reservoir, and the balance held outside the reservoir and adjacent to the inner surface of the closed end of the condom. In an embodiment, the opening of the reservoir may be small enough to prevent entry of the penis and, hence, prevent obliteration of this reservoir space. Composition residing in this reservoir tip is, thus, less likely to be squeezed out during donning of the condom. Additionally, a composition with high viscosity, particularly at low shear rates, with its non-drip and vertical-cling nature, may further prevent loss of the inner surface composition during donning of the condom. During intercourse, the composition in the reservoir may be squeezed out to cover the glans and the distal penile shaft.

In an embodiment, an increased quantity of an inner composition (compared to typical amounts known in the art), having an appropriate rheology as described above is associated with the inner surface of the condom to reduce the tendency of the condom to slip or break. In particular, in an embodiment, a quantity of more than about 0.6 grams, about 1 gram to about 6 grams, or between about 2 to about 3 grams, having a high viscosity at very low shear rates and a moderate viscosity at relatively high shear rates may be used. Such a composition may be relatively adherent in comparison to the lower viscosity of the secretions of the mucosal surfaces of the sexual partner.

An increased quantity of an inner composition having a relatively high viscosity may be used to enable the composition to provide effective coverage over a substantial portion of the penile skin as it spreads in response to movements during intercourse. An increased quantity of the composition may be used to compensate for its resistance to propagation up the shaft of the penis from its initial placement on the inner surface of the closed end of the condom due to its high viscosity. Improving the coverage of the composition at the condom-penis interface increases the degree to which the composition creates a gentle bond between the penile skin and the inner surface of the condom.

Coverage of the penis may increase with increasing quantity of the inner composition. However, if the quantity of the inner composition is excessive, its non-slip function may be compromised. This may occur if propagation of the composition covers the entire area of contact between the condom and the penis, since, in an embodiment, at least a portion of the condom near the base of the penis may be free of the composition.

A second way that an excessive quantity of inner composition may compromise the non-slip character of the condom is by excessively increasing the distance separating the condom and penile skin. This may result in increased "leverage" acting on the inner composition allowing viscous drag on the outside of the condom to move the condom relative to the penis. As found experimentally in Example 3, quantities of an inner composition of about 4 grams and above may compromise the non-slip function of the inner composition.

Use of such an adherent composition may also help prevent semen from propagating over at least a portion of the inner surface of the condom. Liquefied semen has a very low viscosity (see below), thereby increasing the tendency of the condom to slip off the penis if the semen becomes interposed between the condom and penis over a large fraction of the contact area. Pre-existent coverage of a substantial portion of the area inside the condom with an effectively adherent composition reduces the propagation of liquefied semen and, to the extent semen mixes with the composition, increases the viscosity of the semen, reducing the tendency of the condom to slip after ejaculation as shown in the following Example 4.

EXAMPLE 4

The viscosity of freshly liquefied human semen and of various ratios of liquefied semen and BUFFERGEL® were measured with a HADV-III cone and plate viscometer at 25 degrees centigrade at shear rates within the range of the viscometer. Freshly ejaculated human semen was incubated at 37 degrees centigrade for 10 minutes, and experiments completed within two hours of ejaculation. The liquefied semen was measured with a CP40 spindle (appropriate for lower viscosities), and the semen-BUFFERGEL® mixtures were measured with the CP52 spindle (appropriate for higher viscosities). The results are plotted in FIG. 4.

Figure 4:
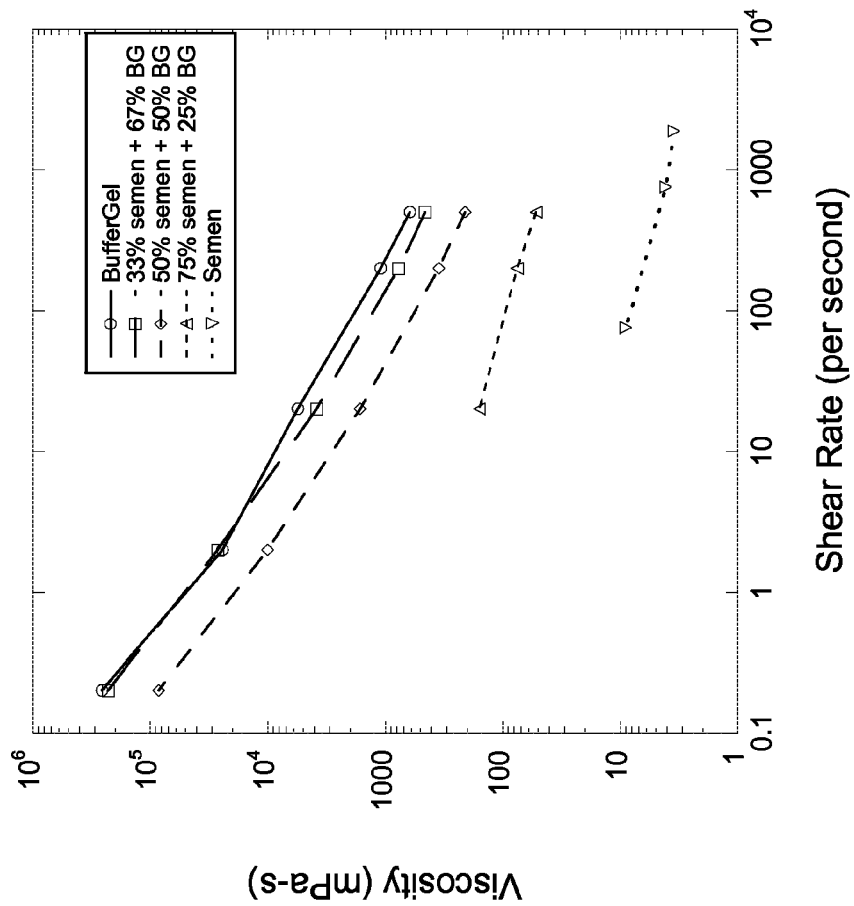
FIG. 4 is a plot comparing log viscosity to log shear rate for semen and mixtures of semen and BUFFERGEL®.

The results demonstrate that liquefied semen is a very low viscosity fluid, having a viscosity at shear rates characteristic of sexual intercourse only about four times higher than water, which has a viscosity of 1 mPa-s at all shear rates. Such a low viscosity fluid may spread widely inside a condom post-ejaculation and may increase the risk of condom slipping. As liquefied semen is mixed with substantial quantities of BUFFERGEL®, an inner composition appropriate for use in the present invention, FIG. 4 shows that the viscosity of the mixture is greatly increased: more than 10-fold when three volumes of semen are mixed with one volume of BUFFERGEL®, and approximately 50-fold when equal volumes of semen and BUFFERGEL® are mixed. It should be appreciated that this increase in viscosity is advantageous to the goal of reducing the tendency of a condom to slip after ejaculation.

In addition to preventing condom slipping by mixing with semen and increasing its viscosity, the inner composition may also act to reduce the area over which semen will propagate inside the condom. The inner composition, adhering to both the penile skin, and the inner surface of the condom, may occupy space, may tend to stay in position, and may substitute its high viscosity for the low viscosity of semen.

In an embodiment, the inner composition may be chosen to have a relatively high viscosity compared to natural mucus secretions, such as saliva or cervicovaginal secretions, or compared to an additional artificial composition applied to the outside of the condom or applied to or otherwise present on the mucosa of the sexual partner that may contact the outside of the condom during use. The viscosity of the adherent inner composition may be substantially greater than that of the natural secretion or added lubricant contacting the outer surface of the condom, measured at a shear rate typical of that experienced during sexual intercourse. Therefore, in an embodiment, the viscosity of the inner composition at shear rates typical for sexual intercourse (500 per second) may be chosen to be substantially greater than the viscosity of cervicovaginal secretions at those shear rates. Since various mucus secretions, including cervicovaginal secretions have a viscosity of approximately 10 mPa-s at a shear rate of 500 per second, in an embodiment, the inner composition may have a viscosity of at least twice this viscosity. Thus, in an embodiment, the inner composition may have a viscosity of at least about 20 mPa-s measured at 500 per second. The non-slip character of the condom may continue to increase as the viscosity of the inner composition is made progressively higher. Thus, in an embodiment, the inner composition may have a viscosity of at least 200 mPa-s, or at least 400 mPa-s measured at a shear rate of approximately 500 per second. However, if the viscosity of the inner lubricant is excessive it may reduce sensation by interfering with subtle motion of the inner surface of the condom relative to the skin. Therefore, in an embodiment, the upper limit of the viscosity of the inner composition may be less than about 10,000 mPa-s at shear rate of 500 per second, less than about 5000 mPa-s, or less than about 2000 mPa-s. Thus, the desirable viscosity range of the inner composition measured at 500 per second may be between about 100 and about 10,000 mPa-s, 200 to about 5,000 mPa-s, or about 400 to about 2,000 mPa-s.

A lubricant on the inner surface of the condom with viscosity higher than that of mucosal secretions on the outer surface of the condom may function to hold the condom's inner surface relatively adherent to the penis, and, if excessive viscosity of the inner composition is avoided, will allow some subtle movement to increase sensation and pleasure. The outer surface, coated with natural secretions, may slip more easily against the sexual partner than against the penis. This may reduce the tendency of the condom to slip off the penis. Furthermore, the reduced viscous drag on its outer surface, such differential slippage may also reduce the risk of condom breakage, since it may reduce the stress placed on the condom that might otherwise cause it to stretch and break.

Therefore, in an embodiment, an adequate quantity of a composition having a relatively high viscosity and bioadhesiveness is disposed on the condom's inner surface to reduce slippage at this surface relative to the slippage at the condom's outer surface to reduce the stresses on a condom that cause slippage or breakage.

In an embodiment, an outer composition may be associated with the outer surface of the condom. In an embodiment, an amount of the outer composition of between about 0.1 and about 1 gram or between about 0.3 and about 0.8 grams may be disposed on at least the outer surface of the condom. In addition to supplementing any insufficiency of natural lubrication to allow comfortable intercourse and to reduce coital trauma, including a lubricant on the outer surface of the condom may contribute to maintaining the condom in place during use. It has been surprisingly found that compositions on opposing surfaces having different viscosities contribute to maintaining the position of the condom on the penis during use. By providing an outer composition that has a viscosity lower than the viscosity of the inner composition at the same shear rate, a differential lubrication effect between the outer surface and the inner surface of the condom may be created to reduce the tendency of the condom to slip off the penis during use. In particular, the viscosity of the outer composition may be at least two-fold lower than that of the inner composition at a shear rate characteristic of sexual intercourse, namely, at 500 per second. Furthermore, in an embodiment, the outer composition viscosity at 500 per second may not be lower than that of mucosal secretions, or about 10 mPa-s. In an embodiment, the outer composition viscosity at 500 per second may not be lower than about 50 mPa-s, or not lower than about 100 mPa-s.

EXAMPLE 5

Figure 5:
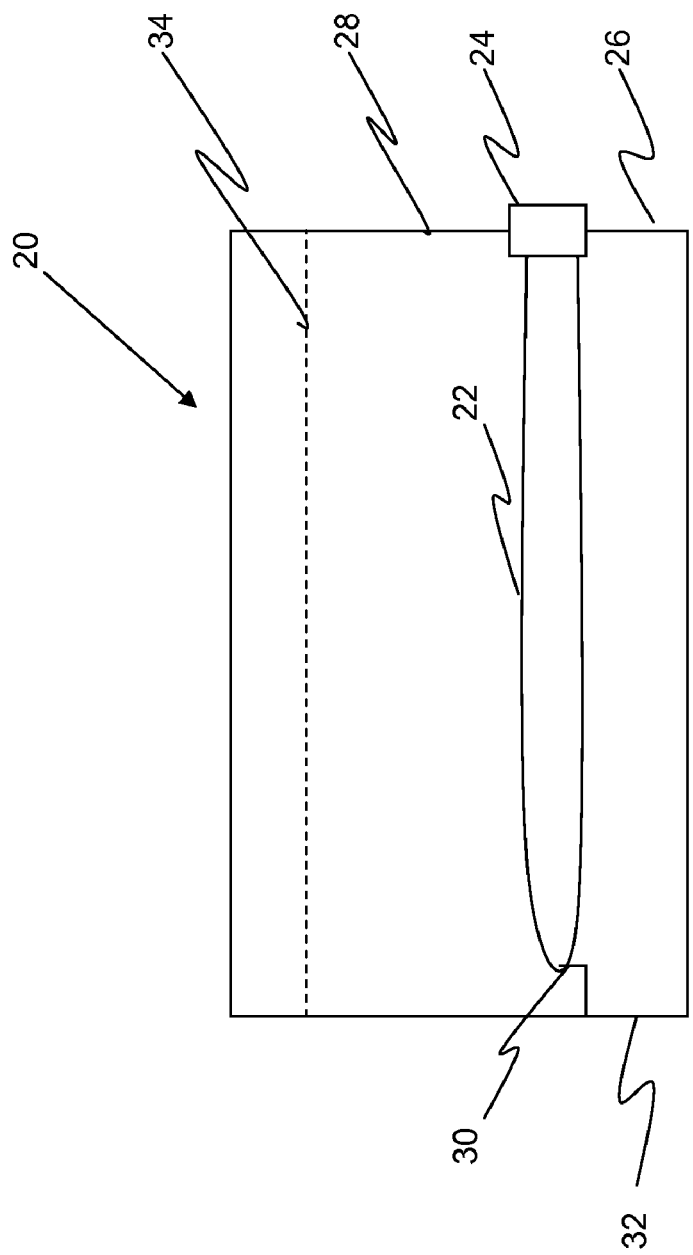
FIG. 5 is a side view of the "artificial vagina" used to test the tendency of condoms to slip after application of various inner and outer compositions described in the present disclosure.

A test of the ability of differential lubrication to reduce the tendency of condoms to slip during use was performed. As illustrated in FIG. 5, a laboratory "artificial vagina" 20 having a vaginal wall composed of a female condom 22 (Reality®, The Female Health Company) was used to perform tests of condom slippage with various combinations of inner and outer compositions with varying viscosities. The female condom 22 was attached by its open end to an opening 24 in one wall 24 of a rectangular tank 28, and suspended horizontally within the tank by attaching its closed end to an attachment point 30 on the inside surface of an opposite wall 32 of the tank 28. To mimic intra-abdominal pressure on the vaginal wall, the female condom was compressed with hydrostatic pressure created by filling the tank with water 34 to a depth of 8 cm above the center of the female condom 22.

An unlubricated condom (TROJAN ENZ® Unlubricated) was placed over a solid plastic cylinder with a diameter of one inch, somewhat less than the inside diameter of the unstretched condom, which is approximately 1.3 inches inside diameter. Use of this size cylinder prevented the elasticity of a stretched condom from contributing to the condom adherence to the cylinder, thus allowing the test to be dependent primarily on the adherence provided by the inner composition. This also made the test somewhat more indicative of the situation of withdrawal after penile detumescence, a circumstance known to be associated with a greater tendency of a condom to slip.

A comparison was made between two compositions having different viscosities at the same shear rate. One composition described above, BUFFERGEL®, having a viscosity of approximately 600 mPa-s at a shear rate of 500 per second, and a viscosity of 27 million mPa-s at 0.001 per second according to FIG. 2 and Table 3 was tested. A second composition tested was a commercially available vaginal lubricant, K-Y® Liquid, which employs hydroxyethylcellulose and glycerin as viscosity generating agents. The viscosity of K-Y® Liquid was measured to be approximately 70 mPa-s at a shear rate of 500 per second, and was estimated to be less than 1000 mPa-s at a shear rate of 0.001 per second by extrapolation of the curve in FIG. 2.

Each composition was applied on either the inner and or outer surface of the condom as indicated in Table 4. The cylindrical penis surrogate was inserted into the artificial vagina and withdrawn at a linear displacement rate of 25 cm per second, corresponding roughly to a shear rate of 500 per second, characteristic of intercourse. In another set of trials, the cylindrical penis surrogate was inserted into the artificial vagina and withdrawn at a linear displacement rate of 2.5 cm per second corresponding to movement of the penis surrogate at this rate corresponds roughly to a shear rate of 50 per second and is relevant to slower movement that may occur during penile withdrawal after intercourse. Movement of the condom on the cylinder was measured and results displayed in Table 4:

TABLE 4

| Trial | Inner composition and quantity | Outer composition | Displacement rate (cm/sec) | Number of repeats | Number of slipping events* |
|---|---|---|---|---|---|
| 1 | None | K-Y ® Liquid | 25 | 10 | 9 |
| 2 | BUFFERGEL ® 0.5 g | K-Y ® Liquid | 25 | 10 | 8 |
| 3 | BUFFERGEL ® 1.0 g | K-Y ® Liquid | 25 | 10 | 2 |
| 4 | BUFFERGEL ® 1.5 g | K-Y ® Liquid | 25 | 10 | 3 |
| 5 | BUFFERGEL ® 2.0 g | K-Y ® Liquid | 25 | 10 | 0 |
| 6 | BUFFERGEL ® 4.0 g | K-Y ® Liquid | 25 | 10 | 3 |
| 7 | BUFFERGEL ® 6.0 g | K-Y ® Liquid | 25 | 10 | 8 |
| 8 | K-Y ® Liquid 0.5 g | BUFFERGEL ® | 25 | 10 | 10 |
| 9 | K-Y ® Liquid 1.0 g | BUFFERGEL ® | 25 | 10 | 10 |
| 10 | K-Y ® Liquid 1.5 g | BUFFERGEL ® | 25 | 10 | 10 |
| 11 | K-Y ® Liquid 2.0 g | BUFFERGEL ® | 25 | 10 | 10 |
| 12 | K-Y ® Liquid 2.0 g | K-Y ® Liquid | 25 | 10 | 10 |
| 13 | None | K-Y ® Liquid | 2.5 | 10 | 5 |
| 14 | BUFFERGEL ® 0.5 g | K-Y ® Liquid | 2.5 | 10 | 0 |
| 15 | BUFFERGEL ® 1.0 g | K-Y ® Liquid | 2.5 | 10 | 1 |
| 16 | BUFFERGEL ® 1.5 g | K-Y ® Liquid | 2.5 | 10 | 0 |
| 17 | BUFFERGEL ® 2.0 g | K-Y ® Liquid | 2.5 | 10 | 1 |
| 18 | BUFFERGEL ® 4.0 g | K-Y ® Liquid | 2.5 | 10 | 2 |
| 19 | BUFFERGEL ® 6.0 g | K-Y ® Liquid | 2.5 | 10 | 7 |
| 20 | K-Y ® Liquid 0.5 g | BUFFERGEL ®® | 2.5 | 10 | 10 |
| 21 | K-Y ® Liquid 1.0 g | BUFFERGEL ®® | 2.5 | 10 | 10 |
| 22 | K-Y ® Liquid 1.5 g | BUFFERGEL ®® | 2.5 | 10 | 10 |
| 23 | K-Y ® Liquid 2.0 g | BUFFERGEL ®® | 2.5 | 10 | 10 |
| 24 | K-Y ® Liquid 2.0 g | K-Y ® Liquid | 2.5 | 10 | 10 |

*Slipping events were defined as movement of the closed end of the condom in excess of 2 cm upon withdrawal of the cylinder from the artificial vagina.

Comparing the results of Trial 1 and Trials 2-7, the application of an appropriate inner composition was shown to reduce slipping events compared to no inner composition, and that differential viscosity of a carbomer inner composition relative to an outer composition with a lower viscosity such as K-Y liquid, is effective in reducing condom slippage against the cylindrical penis surrogate. Furthermore, Trials 2-5 demonstrate a dose-response with increasing quantities of internal composition resulting in generally decreasing degree of condom slipping, demonstrating the value of using an unusually large quantity of an inner lubricant composition. However, as the quantity of internal composition is increased beyond 2 grams, as in Trials 6 and 7, slipping increased both at 4 grams, and even more at 6 grams of BUFFERGEL®. Reversing the positioning of the compositions between opposing surfaces of the condom in Trials 8-12 (as compared to Trials 2-6) indicates that it is the location of the compositions that determines whether slipping occurs, and thus that the degree of slipping is independent of the geometry and the nature of the surfaces in the experimental setup.

Trials 13-24 demonstrate that the results observed at a linear displacement rate of 2.5 cm per second were similar to those of Trials 1-12 at a linear displacement rate of 25 cm per second.

An outer composition, if used, may further be chosen to have an additional rheological characteristic. As previously described, the viscosity of the outer composition may be chosen to be substantially lower than the inner composition at a shear rate of 500 per second. However, in an embodiment, the viscosity at a very low shear rate may be chosen to be sufficiently high as to provide a non-drip and vertical cling character. Such characteristics may be obtained, for example, by the dilution of BUFFERGEL® with normal saline as with the 75% BUFFERGEL® compositions described in Example 1. In an embodiment, the viscosity at a shear rate of 0.001 per second may be at least 2 million. Other formulations that meet these criteria may also be made with components such as cross-linked polyacrylic acid, and other suitable gelling and viscosity-enhancing agents using various formulation combinations including concentration of the gelling agent, pH, and ionic strength. Thus, as with the inner composition, in an embodiment, an outer composition with a high viscosity at low shear rates may be selected to reduce its movement in the package and to reduce the degree to which the outer composition will contact and propagate into the spiral space between layers of the rolled condom. Using compositions with a high viscosity at low shear rates for both the inner and outer lubricants may contribute to maintaining segregation of the compositions to their respective surfaces of the condom in the presence of stresses of packaging, shipping, handling, and use.

In an embodiment, if an outer composition is used, the outer composition may be of a similar osmolality as the inner composition. In addition, concentrations of low molecular weight substances, such as glycerol, propylene glycol, and low molecular weight polyethylene glycols, may be minimized in the compositions of the present disclosure. Nearly all water-based lubricants used on condoms, sexual lubricants and spermicides sold separately from condoms have an osmotic strength much higher than the osmotic strength of intracellular fluids and most other body fluids which is approximately 290 milliosmoles/kg. Without being bound by any particular theory, the relatively high osmolality of these compositions may be due to the common practice of using high concentrations (3-12%) of low molecular weight substances such as glycerol, propylene glycol, and low molecular weight polyethylene glycols which are used for their lubricant, humectant, and for co-solvent properties. Hyperosmolal compositions may draw water from the penile skin, thus diluting the composition, reducing its viscosity, and reducing its adherent nature. If the composition has an osmotic strength that is too high, the composition may have a tendency to be diluted during use by movement of water from the penile skin to the inner adherent composition. Accordingly, in an embodiment the osmotic strength of the compositions provided in the present disclosure may be less than about 600 milliosmolal (milliosmoles per kilogram).

In an embodiment, the composition may be formulated to be hypo-osmotic compared to the osmotic strength of intracellular fluids. Without being bound by any particular theory, a hypo-osmotic formulation may result in loss of moisture from the composition during contact with the skin of the penis causing an increase in viscosity during wear. This may advantageously further increase the tendency of the adherent composition to adhere to the penis during intercourse. Accordingly, in an embodiment, the osmotic strength of the compositions provided in the present disclosure may be approximately 300 milliosmolal or less. If the composition has an osmotic strength that is too low, the composition may become excessively thick, and may be unpleasantly sticky and/or difficult to remove due to excessive water loss from the composition during wear. Accordingly, in an embodiment, the osmotic strength of the compositions provided in the present disclosure may be greater than about 10 milliosmolal and less than about 300 milliosmolal or within the range from about 100 milliosmolal to about 290 milliosmolal.

Various components of the formulation added for other purposes may contribute to the osmotic strength of the composition. For example, preservatives, chelators, physiological salts, and beneficial agents may contribute some osmotic strength. However, as discussed previously, in an embodiment, excessive concentrations of ions in the formulation are avoided to prevent the viscosity from being reduced to a degree that interferes with the proper function of the described disclosure. To this end, non-ionic tonicity adjusting agents may be added to the formulation. For example, small amounts, such as between about 0.1% and about 2% of glycerin or propylene glycol may be added to increase the osmotic strength into the desired isotonic or slightly hypotonic range.

Although making the outer lubricant somewhat hypotonic may also create some tendency for the outer lubricant to be dehydrated by contact with the epithelium of the other sexual partner, this is unlikely to be a significant effect. The quantity of any outer lubricant provided need not be large. Quantities between about 0.2 and about 1 gram may be sufficient to supplement the lubrication of natural secretions. Thus, without being bound by any particular theory, the mucosal secretions on the outside of the condom may dilute this relatively low quantity of outer lubricant, and may minimize any difference in osmolality and tonicity between the outer lubricant and the secretions and the intracellular fluids of the epithelium. Furthermore, the relatively low quantity of outer lubricant may be diluted by the relatively low viscosity mucosal secretions. These factors may prevent the viscosity of the outer lubricant from increasing substantially during use, in contrast to the thickening that may advantageously occur for the inner composition.

The inner and outer compositions associated with the condom of the present disclosure may contain various beneficial agents, including, but not limited to, contraceptive agents, and "microbicides" intended to block the transmission of sexually transmitted pathogens, including Human Immuno-deficiency Virus (HIV). These microbicide agents may include without limitation virucides, blockers of viral entry, or viral replication, bactericides, inhibitors of bacterial replication, acidic buffers, or any other beneficial agent or agents.

Although greater efficacy may be conferred on compositions having limited dilutability, it should be appreciated that an increased mass or volume of an inner composition may allow dilution of more potent agents, thereby limiting toxicity that may be associated with higher concentrations.

Figure 6:
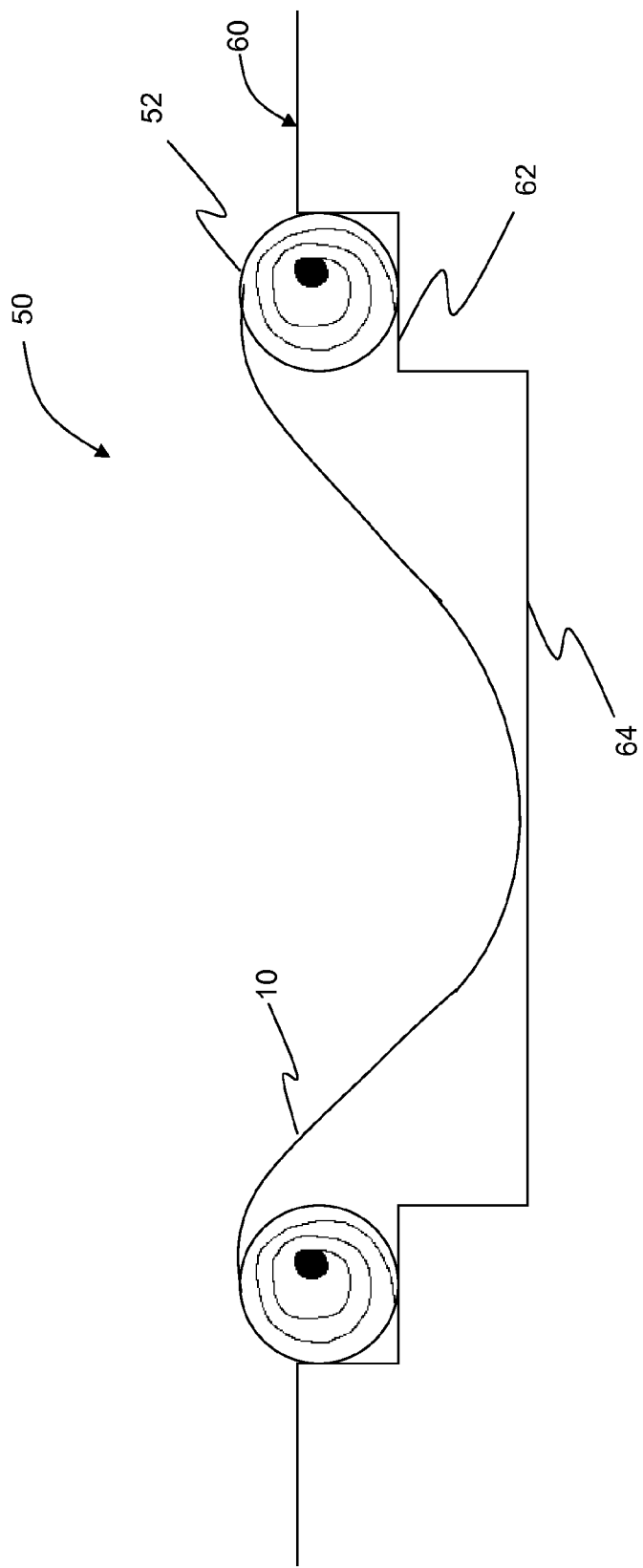
FIG. 6 is a cross-sectional view of a partially rolled condom in a package tray of an embodiment described in the present disclosure.

Referring to FIGS. 6 to 10, the present disclosure also relates to packaging elements such as a kit and methods of packaging to facilitate the packaging of an increased quantity of an inner composition with a condom. The kit and methods are effective to overcome the problems associated with accommodating an increased quantity of inner composition using traditional condom packaging methods. In an embodiment, the inner composition may be applied to the inner condom surface within the circumference of the ring created as the condom is rolled over the majority of its length. The volume of this space may be limited by the dimensions of the ring, and may be further limited since the closed end of the condom may project upward into this space, particularly if air is trapped beneath it as the rolled condom lies on a supporting surface while the inner composition is applied. Therefore, as illustrated in FIG. 6, in an embodiment, a condom package 50 is provided. The rolled ring 52 of the condom 10 is placed upon a closed end support surface such as in a tray 60 with a ring support structure or holding feature, such as, for example, a shelf 62, that holds the ring above a support surface 64 such as the bottom or floor of tray 60. In an embodiment, the holding feature may hold the rolled ring between about 1 and about 10 mm above the support surface 64, or between about 2 and about 5 mm above the support surface 64. The closed end of the condom 10 may be oriented to project downward from the shelf 62 and to contact the support structure 64 as illustrated in FIG. 6. Extending the distance between the ring 52 and the closed end of the condom 10 may provide ample space for both the inner and outer compositions described above. The additional space provided by the suspension of the rolled condom ring 52 above the support structure 64 may increase the capacity to hold the large quantity of the inner composition described in the present disclosure.

The quantity of inner composition may be greater than about 0.6 grams, between about 1 and about 6 grams, or between about 2 and about 3 grams. In an embodiment, a second, outer composition is provided in contact with the outer surface of the closed end of the condom located between the outer surface of the condom 10 and the support structure 64. The quantity of outer composition, if employed is between about 0.1 and about 1 gram or between about 0.3 and about 0.8 grams.

Since one of the goals of an embodiment of the present disclosure is to provide differential lubrication between inner and outer surfaces of the condom, it is advantageous for the inner composition, and any outer composition to be effectively sequestered to their respective inner and outer surfaces of the condom during storage and shipping without cross-contamination. Accordingly, in addition to the features of the compositions themselves, as described above, the present disclosure may include features that further segregate the inner and any outer compositions on their respective intended inner or outer surface of the condom by features of a condom package provided.

Figure 7:
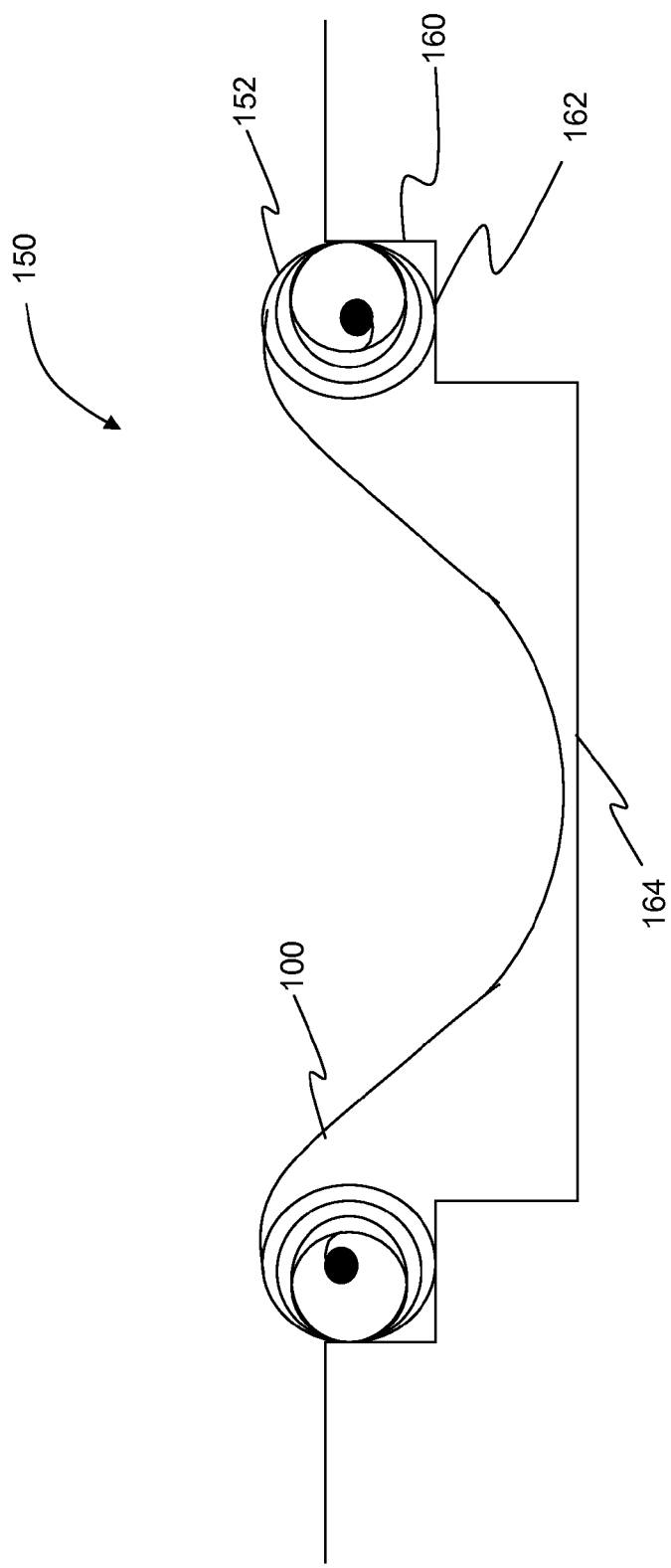
FIG. 7 is a cross-sectional view of a partially rolled condom under compression in a package tray of an embodiment described in the present disclosure.

In an embodiment, package features limit the propagation of either the inner composition or, any outer composition into the spiral space 2 between successive layers of the rolled portion of the condom 100. As illustrated in FIG. 7, in an embodiment, a package 150 may be provided that is adapted to substantially close off the spiral space of the ring 152 of the rolled condom 10 by compression of the ring 152. The package 150 may include a slightly undersized cavity in the tray 164 into which the rolled ring 152 is inserted, thus having the rolled portion circumferentially compressed by a portion of the tray 160.

Figure 8:
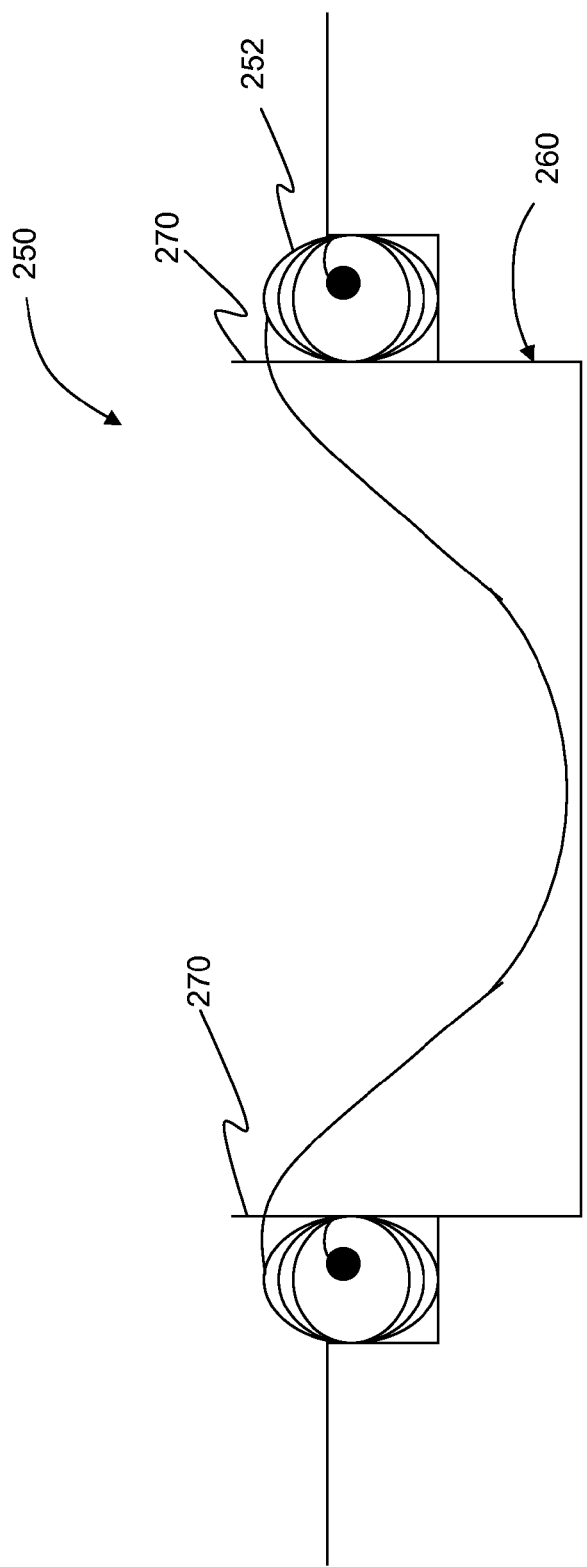
FIG. 8 is a cross-sectional view of a partially rolled condom under compression in a package tray of an embodiment described in the present disclosure.

As illustrated in FIG. 8, in an embodiment, a package 250 may be provided that is adapted to substantially close off the spiral space of the rolled condom 200 by compression of the ring by stretching the rolled ring 252 over an upwardly projecting circular feature 270 of the tray 260.

Figure 9:
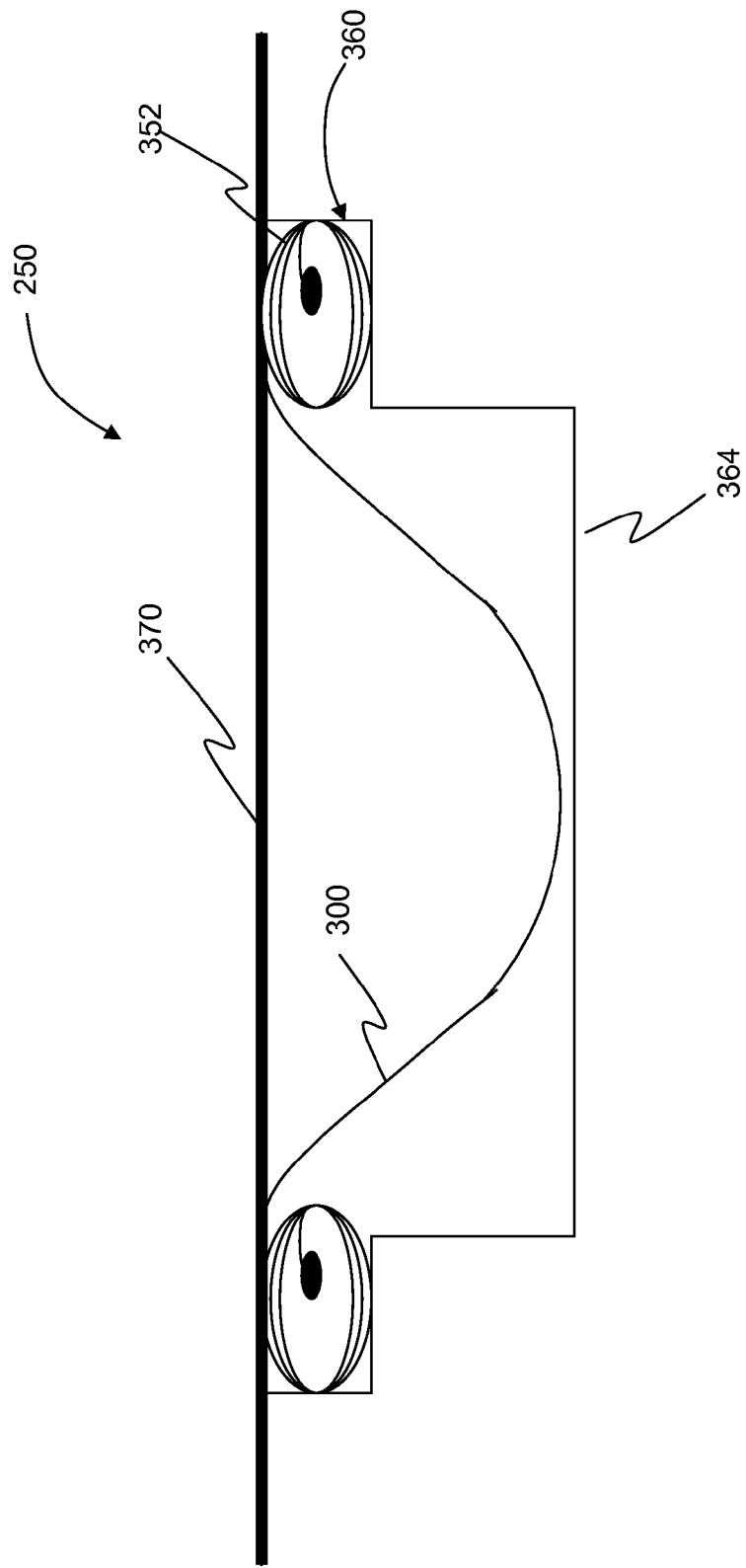
FIG. 9 is a cross-sectional view of a partially rolled condom under compression in a package tray of an embodiment described in the present disclosure.

As illustrated in FIG. 9, in an embodiment, a package 350 may be provided that is adapted to substantially close off the spiral space of the rolled condom 300 by compressing the rolled ring 352 in the vertical dimension between the tray and an additional packaging element 370 placed above the ring 352. In an embodiment, the additional element 370 may include a rigid lid held down in contact with the tray 360 by any suitable functional interlocking means. In an embodiment, the additional element is a lid held in place by introducing a suitable amount of vacuum within the space defined by the tray 360 and the additional element 370.

Figure 10:
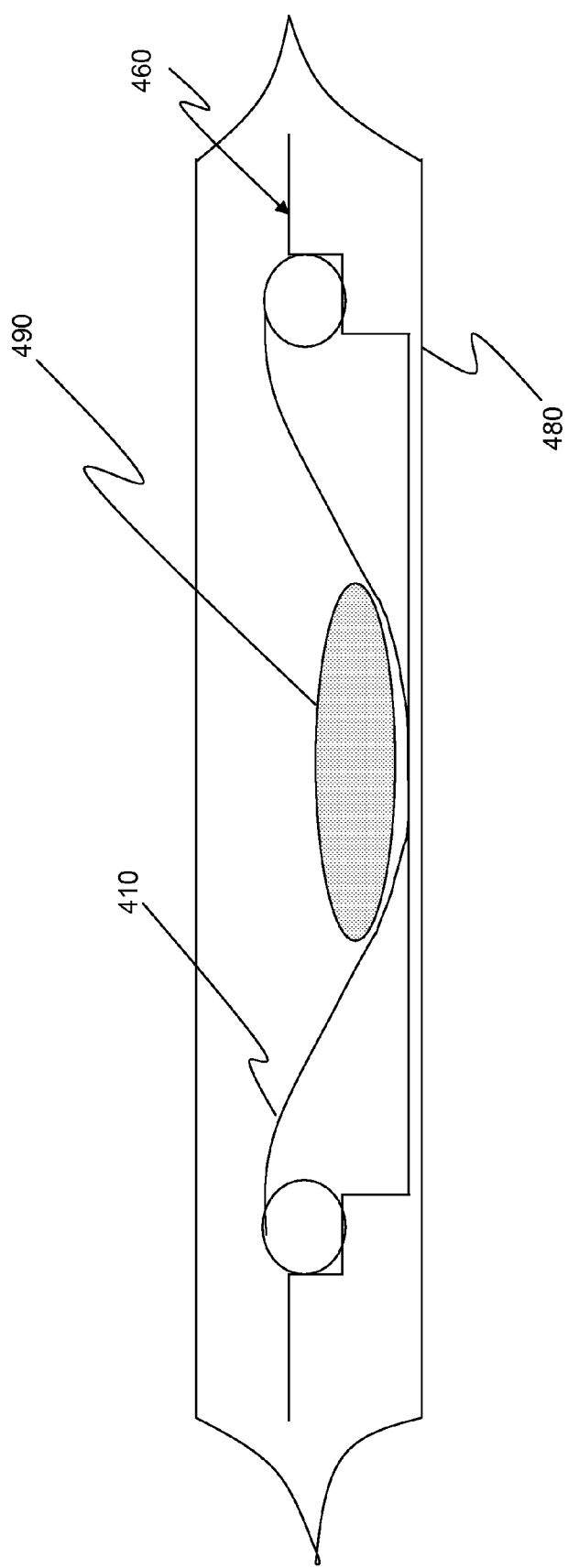
FIG. 10 is a cross-sectional view of a condom, composition, and tray inside a moisture-impermeant secondary package of an embodiment described in the present disclosure.

As illustrated in FIG. 10, in an embodiment, after successively placing any outer lubricant, condom 410, and adherent composition 490 in the tray 460, the tray 460 may be wrapped using conventional condom wrapping materials 480 and machinery, thus applying substantially moisture impermeant other secondary packaging.

In addition or alternatively, in an embodiment, the above-described tray 460 may be combined with any of the other packaging features described above such as additional package element 370 positioned above the condom and applied composition or compositions, and attached to the tray 360 as illustrated in FIG. 9. In this embodiment, the tray 460, the additional package element 370, and any attachment between them may be sufficiently water impermeable to prevent excessive drying of aqueous compositions packaged with the condom. Sufficient water barrier is provided by these elements so that no secondary packaging outside the above-described packages is required to provide adequate shelf life. Water resistant or impermeable components suitable for the tray may include, without limitation, water impermeant plastics such as polyvinylidene chloride (for example Saran®, Dow Chemical) or any other suitable water resistant or impermeable components either alone or in laminates with other plastics, or aluminum. Metal foil laminate structures are also examples of suitable materials for the upper package element. These materials may be chosen to provide a moisture vapor transmission rate of less than 0.01 gram of water per 100 square inches per 24 hours. Various attachment methods may be used including mechanical interlocking, solvent based adhesives, or more preferably heat sealable peelable adhesives or any other suitable method.

In an embodiment, a method is provided where a packaged condom is used to provide an improved means to don a condom. The upper package element 370 or secondary packaging 480 may be removed from the previously described tray 460 that holds the rolled condom. The condom 410 and tray 460 may be applied together to the penile glans without removing the condom 410 from the tray 460 to allow the inner composition to make contact with the glans. The tray 460 may then be removed and the condom 410 unrolled over the glans and shaft of the penis. It should be appreciated that this method may be applied to any of the previously described embodiments. This method is advantageous over other packaged condoms, in that the condom is unambiguously oriented so that the inner surface of the rolled condom will contact the penis and thereby allow the condom to be unrolled without difficulty. In contrast, packaged condoms, where the condom is first removed and then donned, create the possibility for confusion regarding which side of the condom should be applied to the penis.

In an embodiment, a vent is provided to break the vacuum formed by a seal between the condom and the tray that creates suction as the condom begins to come free from the tray as it is applied to the penis, such as when an outer lubricant is disposed between the condom and tray. This would interfere with the easy transfer of the condom to the penis. To prevent this interference, additionally or alternatively, a finger detent is supplied in the outer perimeter of the tray to allow a finger to be inserted under the rolled ring of the condom to prevent or to break any vacuum and to aid in transferring the rolled condom from the tray to the penis.

It should be appreciated that more than one of the above described packaging methods may be combined together within the scope of the present disclosure.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A penile barrier device comprising:
   a condom having an inner surface that is a penis contact surface and an outer surface; and
   a first composition comprising a crosslinked polyacrylic acid and having a viscosity between about 100 and 10,000 mPa-s measured at a shear rate of 500 per second, and a viscosity of at least about 2 million mPa-s measured at a shear rate of 0.001 per second, wherein more than one gram and less than four grams of said first composition is disposed along at least a portion of the inner surface of said condom, the first composition reducing slippage of the device from a penis during use.

2. The penile barrier device of claim 1, which includes a second composition disposed along at least a portion of the outer surface of the condom, wherein said second composition has a viscosity of less than about half the viscosity of said first composition measured at a shear rate of 500 per second.

3. The penile barrier device of claim 2, wherein the second composition has a viscosity of at least 2 million measured at a shear rate of 0.001 per second.

4. The penile barrier device of claim 1, wherein the first composition has a viscosity between about 200 and 5,000 mPa-s measured at a shear rate of 500 per second.

5. The penile barrier device of claim 1, wherein the first composition has a viscosity between about 400 and 2,000 mPa-s measured at a shear rate of 500 per second.

6. The penile barrier device of claim 1, wherein the first composition has an osmotic strength of less than about 600 mOsm.

7. The penile barrier device of claim 1, wherein the first composition is in the form of a gel.

8. The penile barrier device of claim 1, wherein the composition includes an acid buffer.

9. The penile barrier device of claim 1, wherein the crosslinked polyacrylic acid includes a carbomer.

10. The penile barrier device of claim 1, wherein the first composition includes an agent selected from the group consisting of a contraceptive, a microbicide, a lubricant and combinations thereof.

11. A kit comprising:
- a condom having an open end and a closed end at opposing ends of a length of the condom, with an inner surface and an outer surface, wherein the open end of said condom is rolled over a substantial portion of its length to form a condom ring having a circumference;
- a first composition comprising a crosslinked polyacrylic acid and having a viscosity of between 100 and 10,000 mPa-s measured at a shear rate of 500 per second, and a viscosity of at least 2 million mPa-s measured at a shear rate of 0.001 per second, wherein at least one gram and less than four grams of said first composition is disposed on at least a portion of the inner surface of said condom; and
- a package having a cavity defined by a closed end support surface and a ring support structure separated by a separation distance between said closed end support surface and said ring support structure, wherein the closed end of the condom is oriented toward the closed end support surface and said open end of the condom is oriented toward the ring support structure, said ring support structure being adapted to support the condom ring of the open end of the condom in a position at said separation distance from the closed end of the condom, such that the first composition retained on the inner condom surface resists movement within the package; and
- the first composition reduces condom slippage during use.

12. The kit of claim 11, wherein the package includes at least one packaging element adapted to provide circumferential compression of said condom ring.

13. The kit of claim 12, wherein the circumferential compression is directed inward.

14. The kit of claim 12, wherein the circumferential compression is directed outward.

15. The kit of claim 11, wherein the separation distances is between about 1 to about 12 mm.

16. The kit of claim 11, which is removably enclosed within an enclosure package.

17. The kit of claim 11, wherein the closed end support surface forms at least a portion of the enclosure package.

18. The kit of claim 11, wherein the package comprises a material having a moisture vapor transmission rate of less than less than 0.01 gram of water per square meter per 24 hours.

19. The kit of claim 11, which includes a second composition associated with an outer surface of the condom, said second composition having a viscosity of at least 2 million mPa-s measured at a shear rate of 0.001 per second, and a viscosity measured at 500 per second less than half that of said first composition, such that the second composition avoids contact with the spiral space between overlapping layers of the condom in the condom ring.

20. The kit of claim 11, wherein the package is adapted to removably secure the condom to enable a user to position the condom in a proper orientation onto the glans of a penis before removing the package from the condom.

21. A method of reducing slippage of a condom during use comprising:
- providing a composition comprising a crosslinked polyacrylic acid and having a viscosity of between 100 and 10,000 mPa-s measured at a shear rate of 500 per second, and a viscosity of at least 2 million mPa-s measured at a shear rate of 0.001 per second;
- applying more than one gram and less than four grams of the composition on an inner surface of a condom; and
- applying the condom to the penis.

22. The method of claim 21, wherein the composition includes an agent selected from the group consisting of a contraceptive, a microbicide, a lubricant and combinations thereof.

23. The method of claim 21, which includes providing condom packaging adapted to maintain a separation distance between an open end of the condom and a closed end of the condom such that the composition is substantially retained disposed over at least a portion of the inner surface of said condom.

24. A method of reducing slippage of a condom on a penis during sexual intercourse wherein the condom contains at least one gram and less than four grams of a composition associated with an inner surface of the condom in contact with the penis, said method comprising:
- formulating the composition to have a viscosity of between 100 and 10,000 mPa-s measured at a shear rate of 500 per second, and a viscosity of at least 2 million mPa-s measured at a shear rate of 0.001 per second; and
- forming, with the composition, a bond between the penis and the inner surface.

25. The penile barrier device of claim 1, comprising from about 2 g to about 3 g of the first composition.

* * * * *